US006896435B1

(12) United States Patent
Rink

(10) Patent No.: US 6,896,435 B1
(45) Date of Patent: May 24, 2005

(54) FLOATING BAR SOAP

(76) Inventor: James W Rink, 18241 Little Prairie Rd., Prairieville, LA (US) 70769

( * ) Notice: Subject to any disclaimer, the term of this patent is extended or adjusted under 35 U.S.C. 154(b) by 0 days.

(21) Appl. No.: 10/862,608

(22) Filed: Jun. 7, 2004

(51) Int. Cl.[7] .......................... A45D 40/20; A61K 7/50

(52) U.S. Cl. ......................... 401/88; 510/143; 510/144

(58) Field of Search ............................. 401/49, 52, 88; 510/141, 143, 144, 145, 146, 294, 455; 264/251, 264/252, 260, 261, 271.5, 275

(56) References Cited

U.S. PATENT DOCUMENTS

| | | | | |
|---|---|---|---|---|
| 488,393 A | * | 12/1892 | Jewett | 401/19 |
| 821,245 A | | 5/1906 | Hutchinson | |
| 1,083,571 A | | 1/1914 | Waltke | |
| 2,007,107 A | * | 7/1935 | Bottrill | 601/154 |
| 2,468,192 A | * | 4/1949 | Gennusa | 206/77.1 |
| 2,613,185 A | | 10/1952 | Marshall | |
| 2,988,841 A | | 6/1961 | Seufert et al. | |
| 3,076,298 A | | 2/1963 | Tundermann | |
| 3,293,684 A | | 12/1966 | Tundermann | |
| 3,359,206 A | | 12/1967 | Cratsa | |
| 3,413,230 A | | 11/1968 | Dupuis | |
| 3,796,685 A | | 3/1974 | Allen | |
| 4,062,792 A | | 12/1977 | McNabb | |
| 4,181,695 A | | 1/1980 | Rickert | |
| 4,277,358 A | | 7/1981 | Hopkins | |
| 4,309,014 A | | 1/1982 | Blaszkowski | |
| 5,071,583 A | * | 12/1991 | Martell | 510/143 |
| 5,221,506 A | | 6/1993 | Dulin | |
| 5,492,644 A | * | 2/1996 | Minkin | 510/143 |
| 5,857,792 A | | 1/1999 | Iffinger | |
| 5,869,437 A | | 2/1999 | Wolfersberger | |
| 6,555,509 B2 | | 4/2003 | Abbas et al. | |

* cited by examiner

*Primary Examiner*—David J. Walczak
(74) *Attorney, Agent, or Firm*—David L. Ray

(57) ABSTRACT

A slip-resistant floating bar soap having two outer convex-shaped layers of soap connected to an inner layer of concave-shaped rigid water-impermeable buoyant material having an exposed slip-resistant outer surface extending around the outer perimeter of the floating soap bar to provide a gripping surface for the hand of the user to aid in preventing the floating soap bar from slipping from the hands of the user.

9 Claims, 3 Drawing Sheets

FLOATING BAR SOAP

BACKGROUND OF THE INVENTION

1. Field of the Invention

The present invention relates to bar soap such as bath soap. More particularly, the present invention relates to bar soap which floats.

2. Description of the Related Art

When using bar soap to wash oneself or another object in a bathtub or other reservoir of water, the bar soap becomes slippery and can easily be dropped from the hands of the user. Common bar soap will then sink to the bottom of the tub of water. Retrieving the bar soap from the bottom of the bathtub or other body of water is often difficult, inconvenient and time-consuming. The slippery surface and sides of the bar soap contribute to the difficulty of grasping and retrieving the bar soap bar with the wet hand of the user.

Some floating soap bars have small air bubbles entrapped therein. Although such bars will float, the resulting soap bar will be less dense. Lower density of the soap will cause the soap bar to be depleted rapidly.

Exemplary of the related art are the following U.S. Pat. Nos. 6,555,509 B2; 5,869,437; 5,857,792; 5,221,506; 4,309,014; 4,277,358; 4,181,695; 4,062,792; 3,796,665; 3,413,230; 3,359,206; 3,293,684; 3,076,298; 2,988,841; 2,613,185; 1,083,571; and 821,245.

BRIEF SUMMARY OF THE INVENTION

In accordance with the present invention there is provided a slip-resistant floating bar soap having two outer convex-shaped layers of soap connected to an inner layer of concave-shaped rigid water-impermeable buoyant material having an exposed slip-resistant outer surface extending around the outer perimeter of the floating soap bar to provide a gripping surface for the hand of the user to aid in preventing the floating soap bar from slipping from the hands of the user.

The floating bar soap of the invention has the advantage of floating rather than sinking when placed in a bathtub or other water reservoir.

The floating bar soap of the invention has the additional advantage of having a slip-resistant outer edge extending completely around the bar soap to reduce slipping of the bar soap from the hand of the user.

DETAILED DESCRIPTION OF THE INVENTION

Figure 1:
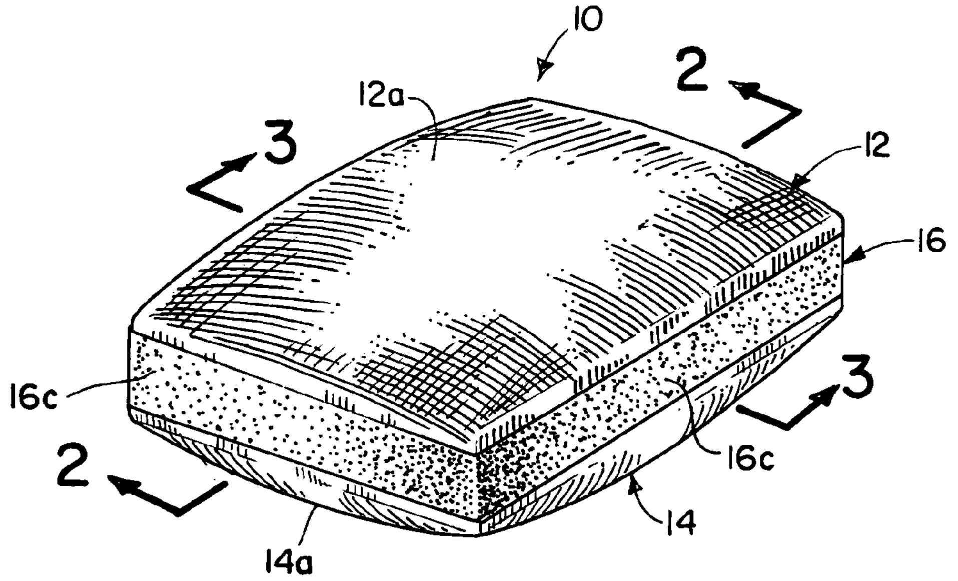
FIG. 1 is a perspective view of the floating bar soap of the invention.
Figure 2:
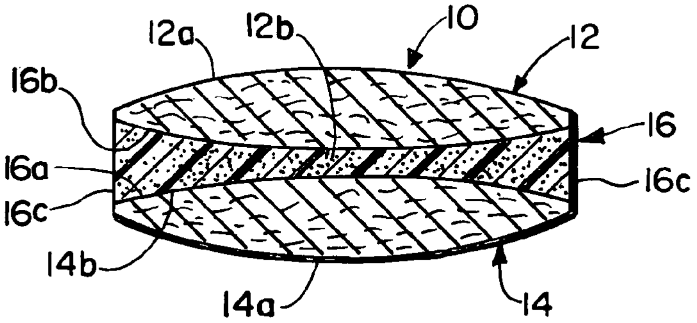
FIG. 2 is a cross-sectional taken along lines 2—2 view of FIG. 1.
Figure 3:
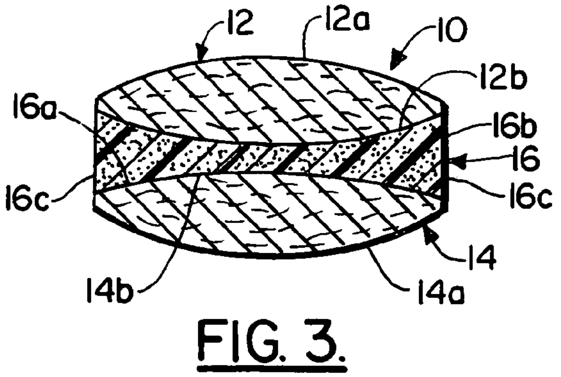
FIG. 3 is a cross-sectional taken along lines 3—3 view of FIG. 1.

Referring now to the drawings, in FIGS. 1–3 the floating bar soap of the invention is generally indicated by the numeral 10. Floating bar soap 10 has two outer layers generally indicated by the numerals 12 and 14 made of soap having a specific gravity of greater than one and an inner layer shown in FIGS. 1–3 and 6 generally indicated by the numeral 16 made from a buoyant material having a specific gravity of less than one. Outer layers 12 and 14 are generally rectangular in shape at the outer edges thereof. If desired, the outer edges of outer layers 12 and 14 could be a straight line.

Soap layers 12 and 14 are made from common bath soap well known in the art. Such common bath soap has a specific gravity of greater than one and therefore will not float on water. Soap layers 12 and 14 are preferably substantially identical in size and shape. Soap layer 12 has a convex outer surface 12*a* and an opposite convex inner surface 12*b*, and soap layer 14 has convex outer surface 14*a* and an opposite convex inner surface 14*b*.

Located between soap layers 12 and 14 is buoyant layer 16. Buoyant layer 16 must be rigid, water-impermeable, and have a specific gravity of less than one. Buoyant layer 16 has concave opposite outer surfaces 16*a* and 16*b* which contact and receive the convex inner surfaces 12*b* and 14*b* of soap layers 12 and 14. Receipt of the convex inner surfaces 12*b* and 14*b* of soap layers 12 and 14 in the concave outer surfaces 16*a* and 16*b* of buoyant layer 16 to which they are bonded increases the horizontal shear force necessary to separate two adjacent layers 12 and 16, or 14 and 16, of bar soap 10.

Figure 5:
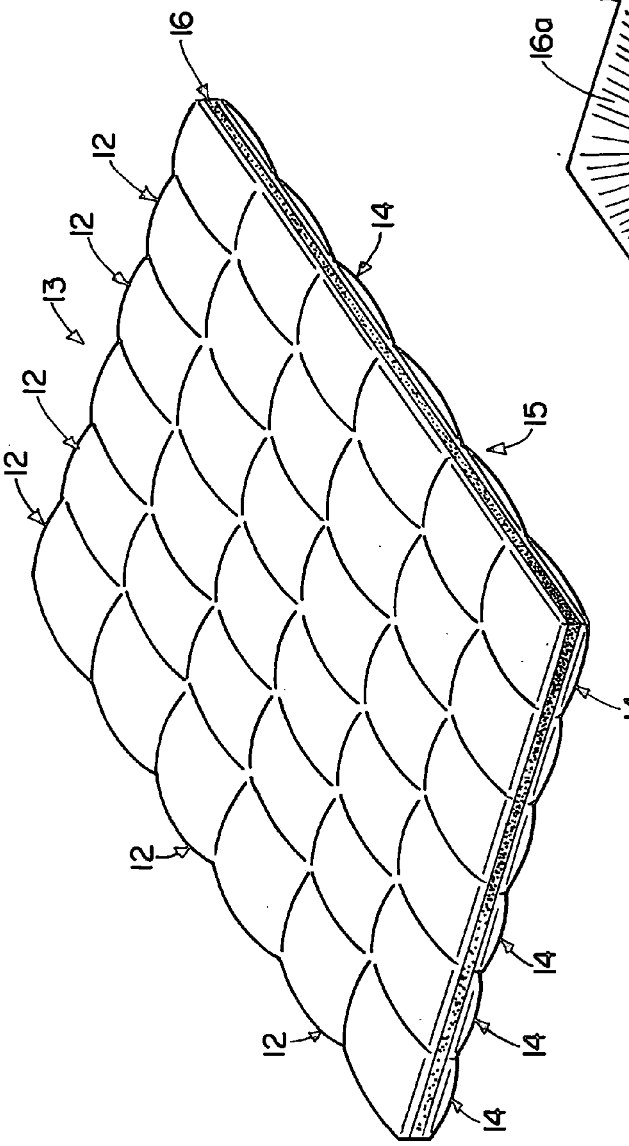
FIG. 5 is a perspective view of two sheets of soap bars of the invention after buoyant material has been injected therebetween.
Figure 6:
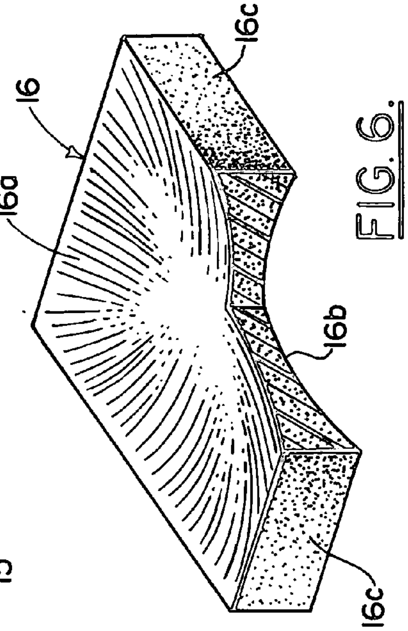
FIG. 6 is a perspective view of the buoyant material injected between to layers of soap.

Buoyant layer 16 has outer edges 16*c* which provide an exposed gripping surface on the outer edges of floating soap bar 10 for grasping or gripping by the hand of the user of floating bar soap 10 to aid in preventing floating soap bar 10 from sliding or slipping from the hand of the user. As shown in FIGS. 1, 5, and 6, outer edges 16*c* of buoyant layer 16 are preferably generally rectangular in shape.

Preferably the maximum thickness or height of outer edges 16*c* of buoyant layer 16 is from about one-fourth to about one-half of the maximum vertical thickness of the floating soap bar 10 shown in FIGS. 1–3 to provide an adequate gripping surface area for the user of floating soap bar 10. Preferably, the thickness of buoyant layer 16 at the midpoint between opposite outer edges 16*c* is about one-eighth to about one-fourth of the maximum vertical thickness of the floating bar soap 10 shown in FIGS. 1–3 to insure an adequate degree of concavity to maximize the volume of soap in outer layers 12 and 14 of floating bar soap 10 and to increase the shear force necessary to separate outer layers 12 and 14 from buoyant layer 16.

Buoyant layer 16 is preferably made from a water-impermeable foamed low density closed-cell polymeric material having a specific gravity of less than one. Exemplary of such foamed polymeric materials well known in the art are foamed polystyrene, polyurethane, and the like. Foamed polystyrene is preferred.

Figure 4:
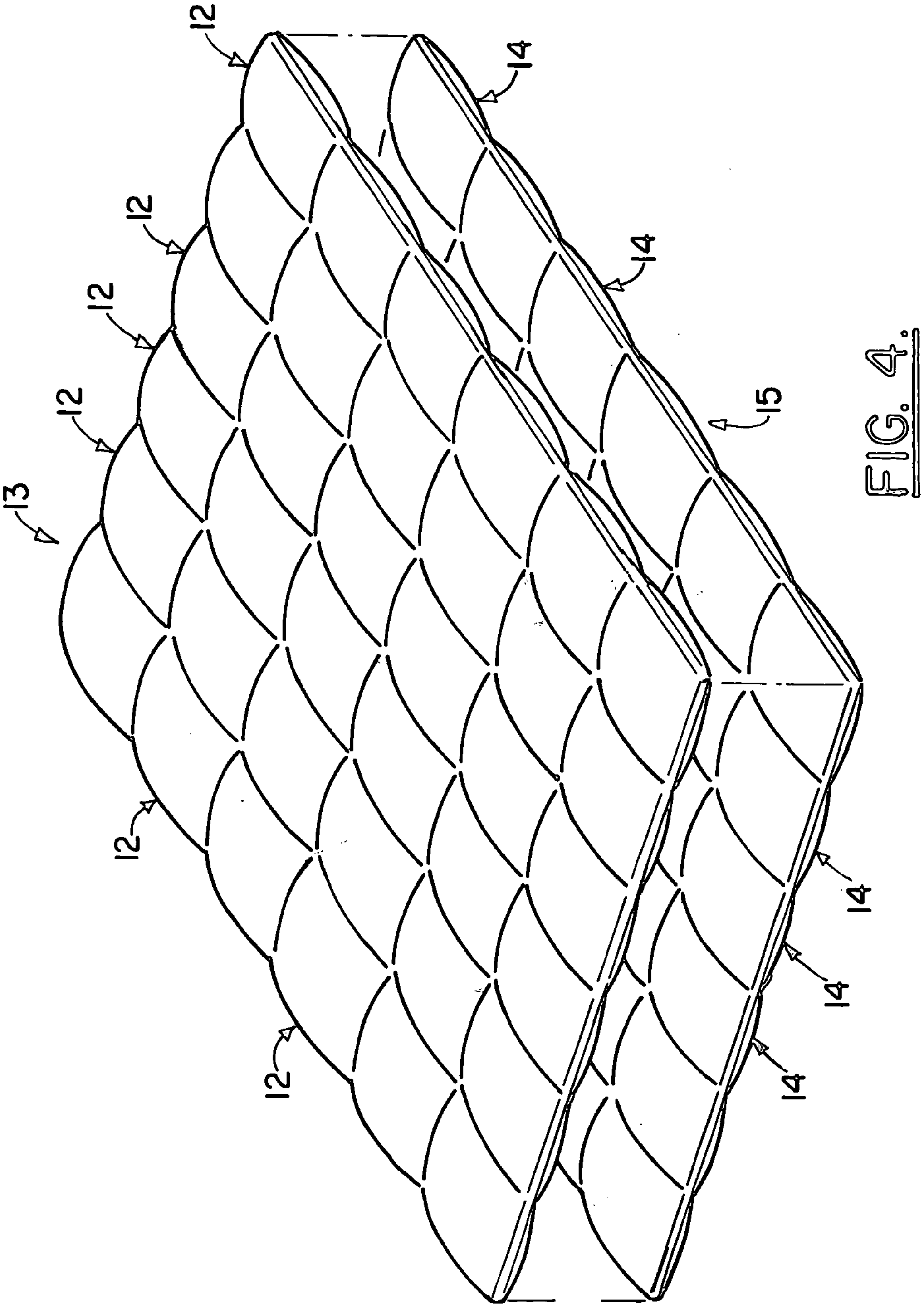
FIG. 4 is a perspective view of two sheets of soap bars of the invention aligned for injection of buoyant material therebetween.

As shown in FIGS. 4 and 5, a preferred method of making the floating bar soap 10 of the invention includes molding, pressing, and/or stamping two substantially identical sheets generally indicated by the numerals 13 and 15 of soap layers 12 and 14, with individual soap layers 12 in sheet 13 being joined at their peripheral edges and individual soap layers 14 in sheet 15 also being joined at their peripheral edges. The inside surfaces of each sheet 13 and 15 may be textured to improve bonding between soap layers 12 and 14 and the buoyant layer 16. By texturing is meant that small irregularities or depressions are molded in the inside surfaces of individual soap layers 12 and 14 in sheets 13 and 15. The size of each sheet 13 and 15 will be selected to eliminate sagging of the sheets when supported at their edges.

The outer surface of each sheet 13 and 15 may be molded or stamped to include a brand name or logo. The convex, sloping outer surface of floating bar soap 10 provides a shape that is more easily held in the hand of the user.

Sheets 13 and 15 are aligned as shown in FIG. 4 and held apart to form a space between sheets 13 and 15 ranging from one-eighth to one-fourth of the total thickness of floating bar soap 10, and a water-impermeable foamed low density closed-cell polymeric material having a specific gravity of less than one is injected between sheets 13 and 15. Preferably, the water-impermeable foamed low density closed-cell polymeric material is polystyrene.

After the water-impermeable foamed low density closed-cell polymeric material has fully expanded and hardened to form buoyant layer 16 between sheets 13 and 15, the individual soap bars 10 will be separated by a band saw with multiple blade, piano wire saw with multiple wires, or other apparatus known in the art.

Floating bar soap 10 has a specific gravity of less than one and preferably a thickness of about one inch. Preferably, floating bar soap 10 is generally rectangular in shape and is from two to three inches in width and three to four inches in length. If desired, floating bar soap 10 could be generally elliptical or oval in shape.

Although the preferred embodiments of the invention have been described in detail above, it should be understood that the invention is in no sense limited thereby, and its scope is to be determined by that of the following claims:

What is claimed is:

1. A slip-resistant three-layer floatable bar soap having a specific gravity of less than one, said slip-resistant three-layer floatable bar soap comprising:

a. a first layer of soap having a specific gravity of greater than one, said first layer of soap having an inner side and an outer side, said inner side of said first layer having a convex surface and said outer side of said first layer having a convex surface, b. a second layer of soap having a specific gravity of greater than one, said second layer of soap having an inner side and an outer side, said inner side of said second layer having a convex surface and said outer side of said second layer having a convex surface, said second layer of soap having substantially the same shape and size as said first layer of soap, and c. a layer of rigid water-impermeable buoyant material having two substantially identical opposite sides and generally rectangular edges extending around the perimeter of said two substantially identical opposite sides, said layer of rigid water-impermeable buoyant material being located between said first layer of soap and said second layer of soap and extending to the border of said first and said second layer of soap, said layer of rigid water-impermeable buoyant material having a first concave outer surface on one of said opposite sides of said rigid water-impermeable buoyant material and a second concave outer surface on the other of said opposite sides of said rigid water-impermeable buoyant material, said convex surface of said inner side of said first layer of soap being received in said first concave outer surface of said layer of rigid water-impermeable buoyant material, and said convex surface of said inner side of said second layer of soap being received in said second concave outer surface of said layer of said rigid water-impermeable buoyant material.

2. The slip-resistant three-layer floatable bar soap of claim 1 wherein said rigid water-impermeable buoyant material is a foamed low density closed-cell polymer.

3. The slip-resistant three-layer floatable bar soap of claim 2 wherein said polymer is polystyrene.

4. The slip-resistant three-layer floatable bar soap of claim 1 wherein the maximum height of said generally rectangular edges of said layer of rigid water-impermeable buoyant material is from about one-fourth to about one-half of the maximum thickness of said floatable bar soap.

5. The slip-resistant three-layer floatable bar of soap of claim 4 wherein the thickness of said layer of rigid water-impermeable buoyant material at the midpoint between said generally rectangular edges extending around the perimeter of said two substantially identical opposite sides is about one-eighth to about one-fourth of the maximum vertical thickness of said floatable bar soap.

6. A method for making slip-resistant three-layer floatable bar soap having a specific gravity of less than one, the method comprising:

a. forming a first sheet of a plurality of adjacent individual first layers of soap joined at their edges and having a specific gravity of greater than one, said first layers of soap having an inner side and an outer side, said inner side of said first layers of soap having a convex surface and said outer side of said first layers of soap having a convex surface, b. forming a second sheet of a plurality of adjacent individual second layers of soap joined at their edges and having a specific gravity of greater than one, said second layers of soap having an inner side and an outer side, said inner side of said second layers of soap having a convex surface and said outer side of said second layers of soap having a convex surface, said second layers of soap having substantially the same shape and size as said first layers of soap, c. aligning said first sheet with said second sheet, d. holding said first sheet apart from said second sheet a selected distance, e. injecting a water-impermeable foamed closed-cell polymeric material having a specific gravity of less than one between said first sheet and said second sheet to bond said first sheet to said second sheet and form a sheet of multiple individual bar soap joined at their edges, f. allowing said water-impermeable foamed closed-cell polymeric material having a specific gravity of less than one to harden, and g. separating adjacent individual bar soap by cutting said edges joining said individual bar soap.

7. The method of claim 6 wherein said selected distance is from one-eighth to one-fourth of the total thickness of said floating bar soap.

8. The method of claim 6 wherein said polymeric material is polystyrene.

9. The method of claim 6 wherein said cutting is performed by a saw having multiple blades.

* * * * *